US006673243B2

(12) United States Patent
Srinivasan et al.

(10) Patent No.: US 6,673,243 B2
(45) Date of Patent: Jan. 6, 2004

(54) PLUG FLOW ANAEROBIC DIGESTER

(75) Inventors: Vadake R. Srinivasan, Baton Rouge, LA (US); John J. Sansalone, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 09/919,710

(22) Filed: Aug. 1, 2001

(65) Prior Publication Data

US 2003/0034300 A1 Feb. 20, 2003

(51) Int. Cl.$^7$ .................................................. C02F 3/00
(52) U.S. Cl. ..................... 210/532.2; 210/601; 210/603; 210/613
(58) Field of Search ................................ 210/613, 601, 210/532.2, 603

(56) References Cited

U.S. PATENT DOCUMENTS

| | | | |
|---|---|---|---|
| 4,246,099 A | | 1/1981 | Gould et al. ................. 210/603 |
| 4,604,206 A | | 8/1986 | Sullivan ...................... 210/603 |
| 4,885,094 A | * | 12/1989 | Srinivasan et al. .......... 210/610 |
| 5,637,219 A | | 6/1997 | Robinson et al. ............ 210/603 |
| 5,792,384 A | * | 8/1998 | Warren ........................ 106/740 |
| 5,863,434 A | | 1/1999 | Massé et al. ................. 210/603 |
| 5,885,540 A | * | 3/1999 | Fulmer et al. ............... 423/311 |
| 6,190,548 B1 | * | 2/2001 | Frick .......................... 210/170 |
| 6,254,775 B1 | | 7/2001 | McElvaney .................. 210/603 |

OTHER PUBLICATIONS

Denn, Morton, "Process Fluid Mechanics," Prentice–Hall, 1980, p. 112.*
Hawkes, F.R. et al., "Chapter 12: Anaerobic Digestion," in Basic Biotechnology (J. Bu'Lock and B. Kristiansen, eds.) pp. 337–358, (Academic Press, Orlando, Florida, 1987).
Metcalf & Eddy, Inc., Wastewater Engineering, 3$^{rd}$ Edition, revised by G. Tchobanoglous and F.L. Burton, especially Chapter 8: "Biological Unit Processes," pp. 359–444 (1991).
Metcalf & Eddy, Inc., Wastewater Engineering, 3$^{rd}$ Edition, revised by G. Tchobanoglous and F.L. Burton, especially Chapter 12: "Design of Facilities for the Treatment of Disposal of Sludge," pp. 765–926 (1991).
Coleman, E., "Wastewater Treatment: A Coastal Challenge," Coast & Sea, vol. 8, pp. 8–11, Fall (2000).

* cited by examiner

Primary Examiner—Chester T. Barry
(74) Attorney, Agent, or Firm—André J. Porter; John H. Runnels; Bonnie J. Davis

(57) ABSTRACT

A simple, reliable, inexpensive, and efficient anaerobic digester for treating organic wastes at a shortened residence time is described. The anaerobic digester is a multi-chambered digester that can handle wastewater and sludge in a large volume at a high flow rate. The digester also allows collection of methane gas for use as an energy source. The reactor is based on a sequential series of reaction chambers in a design that does not require internal moving parts. The volume of the chambers is adjusted to control the relative residence time of the waste to select an anaerobic microorganism group or groups that can efficiently digest the waste presented to that chamber. Under most conditions, no addition of bacteria is necessary. The digester works efficiently using microbes native to the waste material. After the reaction chambers and just prior to leaving as effluent, a settling chamber is located to reclaim the microbes and remove additional solids. In one embodiment, the reactor comprises four sequential chambers. However, other chamber numbers and geometries will achieve the same result if the residence time in each chamber is properly adjusted. Neither pH nor temperature needed to be controlled. However, for a higher yield of methane, pH may be controlled from about 6 to about 8.

23 Claims, 1 Drawing Sheet

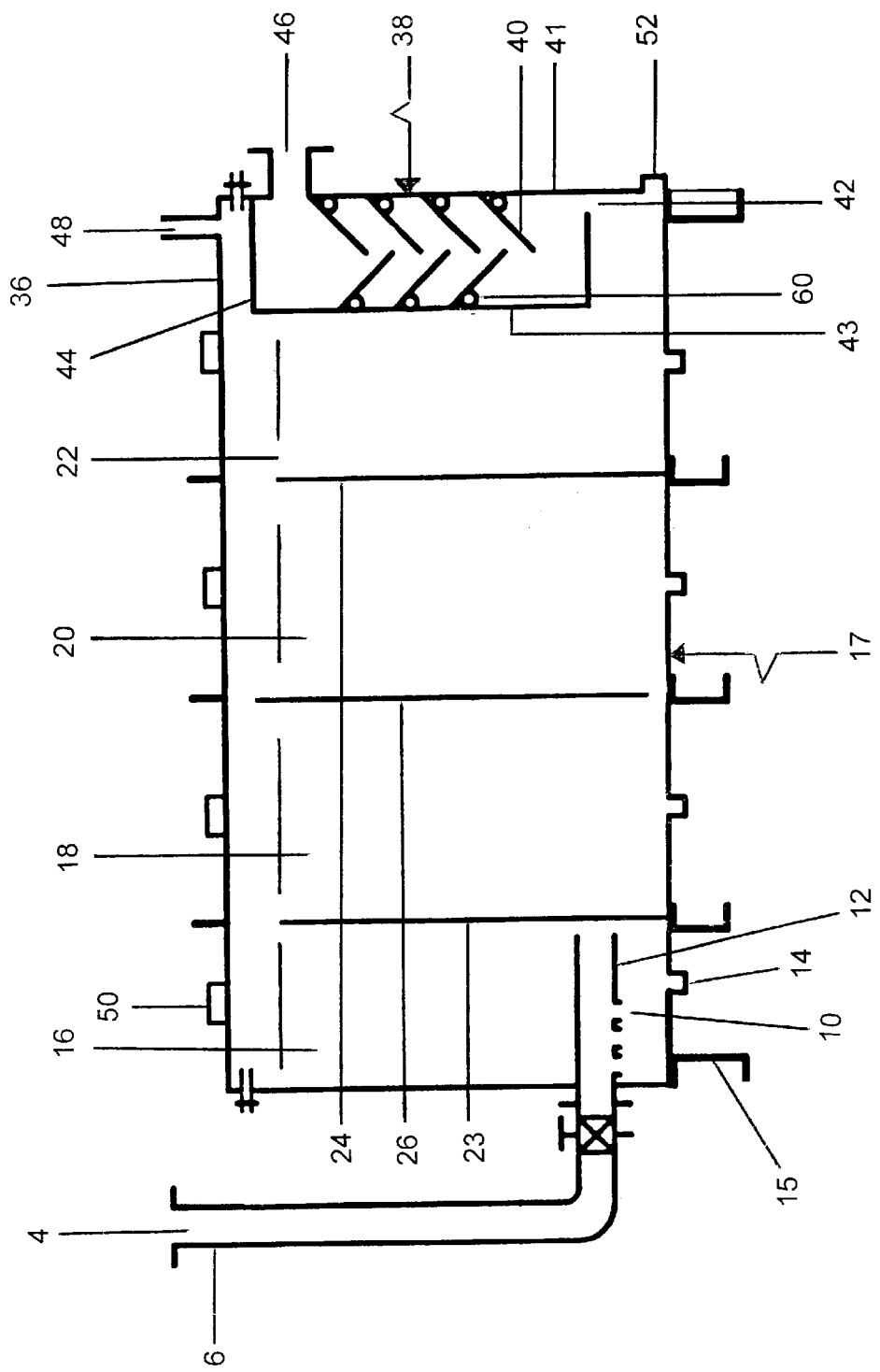
Figure

PLUG FLOW ANAEROBIC DIGESTER

This invention pertains to a simple, inexpensive, anaerobic digester that efficiently and quickly digests primarily organic aqueous and sludge-type wastes using a plug-flow system comprising a series of sequential reaction chambers.

Various designs of digesters exist for the processing and treatment of primarily organic wastes (solids, semi-solids, and liquids) to produce non-hazardous, and sometimes beneficial, products for release to the environment. Digesters may be designed for use in low technology rural areas or for sophisticated industrial areas. Many types of organic wastes (i.e., municipal, industrial, agricultural, and domestic wastes) maybe treated by anaerobic digestion. See F. R. Hawkes et al., "Chapter 12: Anaerobic Digestion," in Basic Biotechnology (J. Bu'Lock and B. Kristiansen, eds.) pp. 337–358, (Academic Press, Orlando, Fla., 1987).

Most digesters are based on either aerobic or anaerobic fermentation, although some combine elements of both. The objectives of all such digestion processes are to reduce the total amount of sludge solids, and to produce a cleaner effluent for discharge to the environment or for further processing prior to discharge. Successful anaerobic digestion of organic wastes usually requires a mixed culture of bacteria with a complex interdependency, terminating in the production of methane by methanogenic bacteria. Hawkes et al., 1987. Waste digesters that use anaerobic processes have at least two advantages over those that use aerobic digestion: (1) anaerobic digestion produces methane, which can be used as a fuel gas either internally or sold commercially; and (2) anaerobic digestion is generally more efficient at removing solids, and thus produces less sludge than aerobic digestion. See U.S. Pat. No. 4,885,094.

The main disadvantage of anaerobic digesters is the long residence time typically required to digest organic waste. Many anaerobic digesters are "batch" or one-stage digesters, e.g., comprising a closed or domed vessel within which very large quantities of organic waste are fermented in batch. Anaerobic batch digesters can take 20 to 30 days to adequately digest the organic solids. See U.S. Pat. No. 5,637,219. Although these batch digesters can handle large quantities of waste, the prolonged time usually required for digestion has limited their use for municipal or industrial waste. As a result, many municipal and industrial wastes are processed using aerobic digestion systems or a combination of aerobic with anaerobic systems. See U.S. Pat. No. 4,885,094.

The microbiology of anaerobic digestion can be generally described as comprising four broad trophic groups, which digest organic materials in sequence. The first group, the hydrolytic and fermentative bacteria, contains both obligate and facultative anaerobes, and removes small amounts of oxygen that may be introduced into the digester with the waste influent. By hydrolysis, this group initially breaks down the more complex molecules (e.g., cellulosics, starch, proteins, lipids, etc.) into smaller units (e.g., amino acids, sugars, and fatty acids). Then, by a process of acidification, this group uses these smaller compounds to produce formate, acetate, propionate, butyrate, hydrogen, and carbon dioxide. These acidic products are then available for the next trophic level. In many digesters, the rate-limiting step is the hydrolysis of complex molecules, particularly the polysaccharides. See F. R. Hawkes et al., 1987.

The second trophic group comprises hydrogen-producing acetogenic bacteria, or proton-reducing bacteria. By a process of acetification (also called "acidification"), this group makes acetate from compounds such as fatty acids, butyrate, formate, and propionate.

The third trophic group of bacteria, comprising homoacetogenic bacteria, produces acetate from hydrogen gas and carbon dioxide. The significance of this group in digester operation is uncertain.

The final trophic group comprises the methanogenic bacteria, which convert compounds such as acetate into methane gas and carbon dioxide in a process called methanogenesis. This group is strictly anaerobic, requiring an oxygen-free environment.

Two important limitations of digesters are the rate at which waste can be processed, and the fraction of solids in the waste that can be digested. The loading rate or flow rate determines the residence time in the digester. The residence time required by standard-rate anaerobic digesters whose contents are unmixed and unheated for the microorganisms to produce a clean effluent is quite long on the order of 30 to 60 days. Optimum anaerobic performance is achieved by proper mixing and heating. Mixing has been achieved by gas injection, mechanical stirring, and mechanical pumping. High-rate digesters whose contents are both heated and mixed have an effective residence time of about 4 days to 15 days, depending on the temperature. The shortest residence time of 4 days was for a temperature of 40° C. See Metcalf & Eddy, Inc., Wastewater Engineering, $3^{rd}$ Edition, revised by G. Tchobanoglous and F. L. Burton (1991), especially Chapter 8: "Biological Unit Processes," pp. 359–444; and Chapter 12: "Design of Facilities for the Treatment and Disposal of Sludge," pp. 765–926.

Wastes are often characterized by the fraction of solids in the waste. One arbitrary classification scheme is low, medium, and high strength wastes, and solid wastes. These four categories can be divided on the basis on dry matter or total solids (TSS) content as corresponding roughly to 0.2–1%, 1–5%, 5–12%, and 20–40% solids by weight, respectively. TSS is also expressed as mg/L, where 20,000 mg/L equals 2% solids. TSS includes both inorganic and organic solids. To measure only organic matter, either a determination of volatile solids is made by combusting all the organic material, or the organic material is chemically oxidized to give a measurement of Chemical Oxygen Demand (COD). See F. R. Hawkes et al., 1987.

Anaerobic digesters include both batch and continuous digesters. A continuous process is usually favored, since the waste is processed continuously, and there is a steady supply of methane. The classic design for industrial digesters is a variant of a one-stage digester, the continuously stirred tank reactor ("CSTR"). In a CSTR digester, all contents are completely mixed. Thus the effluent will contain some amount of freshly added, undigested waste material, and will include some active microbes. The CSTR is usually used for waste with a medium solids content, from 2 to 10% dry matter. Two alternative designs to overcome these problems are the "plug-flow" digester and the microbe retention digester. In a plug-flow digester, the waste passes through the digester in a sequential manner from the inlet to the outlet. The name "plug-flow" is usually used for designs that are unstirred and tubular. The solid material tends to move through the digester sequentially, while the liquid fraction mixes more rapidly. The retention digester is designed to retain the microorganisms in the digester. The most successful design is based on the upflow anaerobic sludge blanket (UASB), in which the waste enters the base of the digester and flows upwards through a sludge of settled bacteria. The treated waste emerges at the top and passes into a zone where any bacteria in the effluent can settle out back into the digester. However, the UASB is only useful with wastes containing low amounts of solids, typically less than 1%. See F. R. Hawkes et al., 1987.

Some anaerobic digesters are considered two-stage digesters, because the processes of hydrolysis and acidification are separated from the processes of acetification and methanogenesis. This separation usually produces methane gas with lower levels of impurities. See U.S. Pat. No. 5,637,219. Complex, multi-stage digesters have been described that spread out the digestive processes into three or more sections. See U.S. Pat. Nos. 4,604,206 and 5,637,219.

In most digesters, bacteria are added to the organic waste, and the temperature is controlled. The bacteria determine the optimum temperature for the digester to operate efficiently. Two common temperature ranges of digesters are a mesophilic temperature range (20° C. to 45° C.) or a thermophilic temperature range (50° C. to 65° C.). Methane production decreases if the optimal temperature range of the methanogenic bacteria is exceeded. See F. R. Hawkes et al., 1987. For example, a maximum volume of methane is produced by mesophilic anaerobic bacteria at a temperature of about 35° C., and by thermophilic bacteria at a temperature of about 55° C. Many digesters also control pH. Methanogenesis is pH dependent, with the optimal pH range from about 6 to about 8.

U.S. Pat. No. 6,254,775 describes an anaerobic digester system based on an upright vessel with internal matrices for bacteria immobilization.

U.S. Pat. No. 5,863,434 describes a process for psychrophilic (low temperature) anaerobic digestion of organic waste comprising the steps of intermittently feeding waste to a single chamber reactor containing sludge previously adapted to organic waste, and allowing the waste to react with the sludge. The waste and sludge eventually settle to form a liquid supernatant zone, which is removed as effluent, and a sludge zone.

U.S. Pat. No. 5,637,219 describes a complex, multi-stage anaerobic digester that is based on an internal rotor assembly that provides for solids mixing and for heat and mass transfer. The digester is divided by the rotor assembly into at least three or more chambers. Initially, the digester is seeded using a mixed population of anaerobic bacteria.

U.S. Pat. No. 4,885,094 describes a temperature-controlled anaerobic digester for low strength organic wastes using anaerobic microorganisms. Anaerobic digestion was accelerated by initially adding a mixture of anaerobic microorganisms, by adjusting the carbon to nitrogen ratio using waste sugar or sugar-containing product, by adjusting the nitrogen to phosphorus ratio if necessary, by controlling the pH between about 6.5 to about 8.0, and by controlling the temperature between about 30° C. to about 50° C. For wastes with 2 to 5% solids, the wastes were pretreated by adding an alkaline solution, heating, or pre-digesting. The main compartments was constructed with alternatively disposed baffles that produced a winding path flow through the compartment.

U.S. Pat. No. 4,604,206 describes a complex anaerobic digester with four different treatment sections to separate the acid-forming and gas-forming phases of anaerobic digestion and the mesophyllic and thermophilic bacteria. In each section is a rotating biological contractor and series of partitions to create zones in which the waste concentration is high and reaction rates are maximized. The digester has multiple internal heaters to control the temperature. The microorganisms in each section are pre-established on fixed media matrices that helps prevent microbial movement from one compartment to the next.

U.S. Pat. No. 4,246,099 describes an aerobic/anaerobic digestion process in which, prior to anaerobic digestion, the sludge is heated and oxygenated to partially decrease the biodegradable volatile suspended solids.

An unfilled need exists for a simple, inexpensive anaerobic digester that can efficiently treat organic waste of higher solids content at a shorter residence time than can conventional anaerobic digesters.

We have discovered a simple, reliable, inexpensive, and efficient anaerobic digester for treating organic wastes at a shortened residence time. The anaerobic digester is a multi-chambered digester that can handle wastewater and sludge in large volumes at a high flow rates, using a plug-flow system. The digester also allows collection of methane for use as an energy source. The reactor comprises a sequential series of reaction chambers in a design that does not mechanically stir and mix the waste as it passes through the digester. The chambers may optionally be contained within a single vessel, in a manner that promotes serpentine flow, or they may comprise separate vessels linked one to another. The volume of the chambers may be selected to control the relative residence times of the waste to select an anaerobic microorganism group or groups that can efficiently digest the waste presented to each chamber. The flow of waste is controlled to ensure that the waste passes through each chamber before exiting. Under most conditions, no deliberate addition of particular bacteria is necessary. The digester works efficiently using the microbes native to the waste material. After the reaction chambers, and just prior to the exit port for the effluent, a settling chamber is located to remove any microbes and additional solids from the effluent. In one embodiment, the reactor comprises four sequential chambers. However, other numbers of chambers and geometries will achieve similar results if the residence time in each chamber is properly adjusted. Neither pH nor temperature was controlled; however, for a higher yield of methane, pH could be controlled from about 6 to about 8.

BRIEF DESCRIPTION OF THE DRAWING

The FIGURE is a side view of one embodiment of a four-chambered anaerobic digester in accordance with the present invention.

This multi-chambered digester provides a series of environments that select for anaerobic microorganisms that efficiently digest sludge and wastewater. Under most operating conditions, no microorganisms will have to be added above those naturally found in the sludge. However, if the organic waste is from an industrial source, e.g., a paper mill, a mixed population of anaerobic microorganisms may need to the added initially. The initial chamber can receive a sugar solution to boost the available carbon source, if the waste has a low carbon concentration, e.g., if the sludge has been pre-digested aerobically. For previously untreated sludge, the sugar addition may prove unnecessary. The digester does not contain either a rotor, another moving mechanical mixer, or gas aerator to mix the contents.

The predominant microorganisms selected in the first chamber are hydrolytic and fermentative bacteria. In the subsequent reaction chambers, increasing percentages of acetogenic and methanogenic bacteria are selected. The volume of the first chamber relative to the sum of the volume of the next two chambers is important, and should be about one-half to one-fourth the sum of the volumes of chambers two and three. Since volume of the chamber determines the relative residence time for any given flow rate, the first chamber will have a two to four times lower residence time than that of chambers 2 and 3. Without wishing to be bound by this theory, it is believed that digestion by the hydrolytic and fermentative bacteria of chamber one is a faster process than either acetogenesis and methanogenesis, the primary processes in chambers 2 and 3. The relative sizes of chambers 2 and 3 to chamber 4 are less important. Methane gas rises to the top of each chamber and can be collected as produced. The production of methane can be estimated by methods known in the art. See Ch. 8, Metcalf & Eddy, Inc. (1991).

By using naturally-occurring microorganisms, and by compartmentalizing the selection of organisms that most effectively thrive on the material found in that particular compartment, the digester efficiently and rapidly digests the waste. This efficiency is surprising because temperature need not be controlled, no bacteria need be added to the sludge, and the contents of the reactor need not be mechanically stirred.

There are several advantages to this simple, plug-flow anaerobic digester. First, the overall size of the digester can be adjusted to handle a wide range of waste volumes, from small volumes (e.g., small communities, coastal communities, small industries, seafood process, etc) to high volumes (e.g., large industries and municipal wastes). Second, the multi-chamber anaerobic digester enables digestion at a high rate, reducing the residence time necessary to produce a clean effluent. Third, the digester requires neither predigestion, heating, nor spiking with bacteria to initiate anaerobic digestion; only an additional carbon source may be needed, depending on the nature of the waste stream. The amount of the carbon addition is based on the carbon content of the waste material. Preferred sources of carbon include waste sugars or sugar-containing products, e.g., glucose or sucrose from a source such as blackstrap molasses, raw sugar, or a crude product from beet or cane processing. Moreover, if the waste source has a low microbe concentration (e.g., some industrial waste), the addition of some microorganisms may be helpful. Finally, this digester is energy-efficient since neither internal moving parts nor heating coils are required. Once the digester is operating and producing a clean effluent, the flow rate can be increased to handle a larger volume of waste material. Without wishing to be bound by this theory, it is believed that a residence time as short as 12 hours can eventually be achieved that produces a clean effluent.

To establish the microorganism populations in the chambers of the digester, organic waste is initially fed to the digester at a flow rate to achieve a residence time of approximately 72 to 96 hours. Steady state is achieved after about five residence times. Once steady state is attained, the flow rate can be increased to achieve an operational residence time of 48 hours, and eventually to a residence time as short as approximately 12 hours.

Steady state is determined by comparing the concentration of organic matter of the influent material with that of the effluent. The amount of organic material maybe measured by the chemical oxygen demand ("COD"). Another parameter of interest is the total suspended solids ("TSS"), which is the total fraction of solids (both organic and inorganic) by weight. Steady state may be defined as an average removal of over 70% of both organic material and suspended solids from the influent.

One Embodiment of a Multi-Chambered Anaerobic Digester

The FIGURE illustrates a side view of one embodiment of a four-chambered, plug-flow serpentine anaerobic digester in accordance with the present invention. This embodiment comprises a lid 36, a bottom 52, an influent tube 4, a gas exit port 48, a reactor 17 and an effluent port 46. The reactor comprises four sequential reaction chambers (first chamber 16, second chamber 18, third chamber 20, and fourth chamber 22) and a settling compartment 38. In a preferred embodiment, all components of the anaerobic digester that make contact with waste and anaerobic microorganisms are made from noncorrosive materials, e.g., stainless steel or concrete, including precast concrete. Corrosion can otherwise occur due to the acidic pH that can form inside the digester. Cementitious materials may be ideal, because calcium carbonate will slowly leach out of the concrete and buffer the acidic pH and help maintain the pH in the optimal range for methanogenesis, from about pH 6 to about pH 8.

As shown in the FIGURE, the influent tube 4 comprises distal end 6 and proximal end 12. In this embodiment, distal end 6 is located adjacent to the anaerobic digester at a height above lid 36 sufficient to prevent the waste from backflowing when the digester is shut down. Alternatively, a valve could be placed on the influent tube 4 to prevent backflow. Proximal end 12 is located inside first chamber 16 near bottom 52.

Wastewater and sludge flow into the first chamber 16 through proximal end 12. In a preferred embodiment, outlets 10 allow small, dense debris (e.g., gravel, etc.) to exit before the proximal end 12, for later removal when the digester has been shut down.

As shown in the FIGURE, first chamber 16 and fourth chamber 22 are smaller and are separated from second chamber 18 and third chamber 20, respectively, by chamber dividers 23 and 24 extending perpendicularly, without a space, from bottom 52. The smaller volumes mean that the residence times in the first and fourth chambers are less than those in the second and third chambers. The distance between the top of chamber dividers 23 and 24, and lid 36 allows the waste material to flow from one chamber into the next chamber and allows methane and carbon dioxide gas to collect at the top. Additionally, the placement of the dividers and the relatively high flow rate prevent any substantial back flow or mixing into the previous chamber.

The second chamber 18 and third chamber 20 are separated by inner chamber divider 26, but are confluent at the bottom. Inner chamber divider 26 extends perpendicularly to a position near bottom 52. The distance between bottom 52 and divider 26 is sufficient to allow the partially digested waste material to flow underneath divider 26 from second chamber 18 into third chamber 20. The space between lid 36 and the top of chamber divider 26 allows gas to flow into third chamber 20. However, divider 26 extends higher than the other two dividers 23 and 24, whose height determines the height of the liquid, partially-digested waste. Thus no waste will flow over the top of divider 26, which means that the waste will flow down through second chamber 18, then under divider 26, and up through third chamber 20, before flowing into fourth chamber 22. This regulated flow through all the chambers ensures that the microorganisms in all chambers will have the opportunity to digest the waste flow.

In a preferred embodiment, lid 36 is removable. Lid 36 contains four sampling ports 50, one located above each chamber. Sampling ports 50 allow easy access to the chambers, providing a means for sampling the contents or for adding various solutions to control pH or add carbon if desired. Additionally, bottom 52 contains four drain ports 14, one in each chamber, which allow emptying and facilitate cleaning of the chambers. Small debris discharged at outlets 10 can also be removed through drain plug 14, located at the bottom of first chamber 16.

Settling compartment 38 comprises an outer wall 41, a divider 43, and a plurality of baffles 40. Divider 43 separates settling compartment 38 from fourth chamber 22. Settling compartment 38 also has a top 44 that is parallel to lid 36. Top 44 serves two purposes: (1) a cover for settling compartment 38, preventing digested influent from flowing out the gas exit port 48; and (2) a channel for gas to escape from inside the digester through gas exit port 48. Gas formed inside settling compartment 38 is passed out with the effluent. Settling compartment 38 is partially closed at the bottom, leaving an opening 42 to allow digested waste material to enter from fourth chamber 22. In a preferred embodiment, a manifold (not shown) is attached to outer wall 41 to provide access to settling compartment 38. The manifold allows emptying of settling compartment 38 when the digester is shut down. Inside settling compartment 38, baffles 40 are mounted to alternate between outer wall 41 and divider 43 and to create a winding path to effluent port 46. The angle between each baffle 40 and the adjacent wall is sufficient to create a settling effect for small undigested material in the effluent flow. The winding effect helps to settle out any microbes or additional solids and produces a cleaner effluent. Baffles 40 will need to be periodically cleaned.

EXAMPLE 1

Anaerobic Digester Prototype

A prototype digester was built from stainless steal to digest primarily wastewater sludge. The main section of the prototype digester, reactor 17, was constructed from a stainless steel tank having inside dimensions of 2.44 m×1.22 m×1.13 m (96 in×48 in×48 in). The working volume of the digester was 3624 L or 958 gal. The tank was mounted onto a steel frame 15.

Four sequential reaction chambers were created by mounting four dividers to the inside walls of the tank. Divider 23 was attached to bottom 52, and extended to a height of 1.1 m (42 in) above bottom 52, forming first chamber 16. Divider 26 was mounted above bottom 52, forming a 0.06 m (2.4 in) spacing between bottom 52 and divider 26. Divider 26 extended to a height of 1.13 m (44.4 in) above bottom 52, forming second chamber 18. Divider 24 was mounted on bottom 52 0.46 m (18 in) from divider 26, forming both third chamber 20 and fourth chamber 22. Both first chamber 16 and fourth chamber 22 had a volume of approximately 0.59 $m^3$ (36,288 $in^3$), while second chamber 18 and third chamber 20 each had a volume of approximately 0.79 $m^3$ (48,384 $in^3$). The influent tube 4 comprised a 0.1 m (4 in) diameter stainless steel pipe attached 0.15 m (6 in) from the bottom 52 of the tank and extended approximately 0.41 m (16 in) into first chamber 16, forming an inlet. Each chamber included a drain port 14 inserted at the center of each chamber through bottom 52.

Divider 43 was mounted 0.20 m (8 in) above bottom 52 and extended to a height of 1.12 m (44 in) above bottom 52, forming settling compartment 38. Three baffles 40, each having a length of 0.23 m (9 in), were attached to divider 43 and mounted on vent tubes 60. The first baffle 40 was mounted 0.32 m (12.5 in) above the bottom end of divider 43.

Consecutive baffles were mounted 0.18 m (7 in) apart. Four baffles 40 were attached to outer wall 41 and mounted on vent tubes 60. The angle between each baffle 40 and the adjacent wall was 45°. The top end of divider 43 was 1.13 m (44.4 in) above bottom 52. Effluent port 46, having a diameter of 0.10 m (4 in), was mounted to the top end of outer wall 41. The center of effluent port 46 was 1.02 m (40 in) above bottom 52.

Lid 36 was fabricated from a 2.44 m×1.22 m (96 in×48 in) sheet of stainless steel. When mounted on top of the steel tank, it created at least a 0.91 m (3.6 in) gas flow channel from each chamber to gas exit port 48. Lid 36 was equipped with 0.10 m (4 in) diameter sampling ports centered over each chamber.

The digester was constructed such that sludge flowed initially into the first chamber 16 from the bottom, while small debris fell through outlets 10. The sludge then ascended and filled the first chamber 16, and eventually flowed over the top end of divider 23 and downward into second chamber 18. Second chamber 18 and third chamber 20 filled almost simultaneously through the opening between bottom 52 and divider 26. Once the level of the material reached the top end of divider 24, sludge then flowed into fourth chamber 22. As the level of material rose in the fourth chamber, material flowed up into settling compartment 38 and eventually out effluent port 46. The level of the sludge in the chambers was controlled by the height of dividers 23 and 24. Once the reactor was full and effluent flowing out port 46, new influent waste would travel up through first chamber 16, down through second chamber 18, up through third chamber 20, down through fourth chamber 22, and finally up through the settling compartment 38 to exit the digester as effluent. Each subsequent chamber receives the waste as digested by the chamber before. Thus the amount of complex molecules is vastly decreased, but the amount of smaller units and organic acids is much greater, once the waste leaves first chamber 16. By the end of third chamber 20 and fourth chamber 22, the primary process is methanogenesis.

EXAMPLE 2

Efficiency of the Multi-Chambered Prototype Anaerobic Digester

The efficiency of the prototype anaerobic digester was tested at the Central Waste Water Plant in Baton Rouge, La. The four-chambered prototype was used to digest a portion of the waste sludge generated by the primary clarifier at the plant. Testing was conducted over a seven month period, from September through the following March.

Every two to three days, measurements were made of pH, alkalinity, temperature, total organic material, dissolved organic material, total suspended solids (TSS), and volatile suspended solids (VSS), following the protocols of Standard Methods for Water and Wastewater Examination, $19^{th}$ Edition, published jointly by the American Public Health Association and the Water Environmental Federation (1995). Total organic material was measured as chemical oxygen demand (COD), using the chromate method. Total organic material measures both insoluble particulate phase material and soluble material. Dissolved organic material, measured as soluble COD, was determined by first passing the sample of either influent or effluent through a 0.45 micron membrane filter. TSS (total suspended solids), representing both inorganic and organic material, was measured by passing the sample through a nominal 1.2 micron glass-fiber depth filter, drying the filter, weighing the filter plus residue, and subtracting to find the weight of the residue on the filter. VSS was determined by combusting the filter at 550° C., weighing the filter after combustion, and subtracting to obtain the amount of volatile material removed by combustion.

During the intial use of the digester, wastewater sludge with approximately 1% (10,000 mg/L) solids was introduced to the digester at a flow rate of 250 gallons per day (GPD), corresponding to an operational residence time of about 72 hr. Steady state was reached after about 360 hr, or about five times the residence time. After achieving steady state, the sludge loading rate was increased to 800 GPD, or a residence time of 30 hr. After four months, the flowrate was increased to 1000 GPD, or a residence time of 24 hr. After about one month, the flow rate was dropped to 500 GPD, or a residence time of 48 hr.

Throughout this experiment, a 10% sucrose solution was added at a constant rate of 10 L/day to influent entering first chamber. Sucrose was thought to help stabilize the growth of microorganisms and increase the rate of fermentation and production of methane. As fermentation and digestion occurred, methane began to accumulate. Accumulated gas exited between the sludge levels and lid 36 through gas exit port 48. No attempt was made to collect the methane during this experiment or to measure the amount produced.

At no time were any microorganisms deliberately added to the sludge (other than those naturally present in the sludge itself), nor was pH or temperature deliberately controlled. The experiment occurred during the months of September through March, when the ambient temperature fluctuated from 30° C. to less than 5° C. However, the influent and effluent temperature range was only from about 10° C. to about 30° C. The TSS of the influent wastes varied from about 0.6% to about 9%. Table 1 compares different measurements for the three residence times of 14, 30, and 48 hr. The measurements in the table are expressed as the mean plus/minus a standard deviation ($\bar{x} \pm S.D.$). The table also gives the total number of samples (N) and the range of values in the samples.

TABLE 1

MEASUREMENTS OF SEWAGE UNDER DIFFERENT FLOW RATES
[$\bar{x} \pm$ S.D.; (N); (range)]

| Parameters Measured | | Residence Time (Hours) (Flow Rate) | | |
|---|---|---|---|---|
| | | 24 (1000 GPD) | 30 (800 GPD) | 48 (500 GPD) |
| pH | Influent | 5.24 ± 0.56 (7) (4.65–6.22) | 5.91 ± 0.81 (8) (5.10–7.22) | 5.99 ± 1.03 (30) (4.65–7.79) |
| | Effluent | 4.66 ± 0.26 (7) (4.22–5.05) | 4.84 ± 0.19 (8) (4.50–5.20) | 4.94 ± 0.47 (30) (4.58–6.42) |
| Alkalinity [mg/L] | Influent | 937.78 ± 129.89 (4) (800.0–1833) | — | 914.14 ± 374.92 (30) (378.7–1759) |
| | Effluent | 730.07 ± 48.84 (4) (674.2–1106) | — | 721.42 ± 270.16 (30) (178.7–1172) |
| Temperature | Influent | 16.96 ± 3.85 (7) (11.30–22.30) | 23.71 ± 4.36 (11) (15.90–28.50) | 29.98 ± 5.03 (26) (21.30–36.20) |
| | Effluent | 10.04 ± 5.71 (7) (0.50–17.90) | 21.07 ± 6.02 (11) (13.30–29.00) | 26.57 ± 5.46 (25) (14.00–33.80) |
| Total COD [mg/L] | Influent | 30188 ± 8947 (8) (14671–122260) | 32292 ± 18328 (22) (12585–82099) | 37282 ± 12800 (30) (19034–85263) |
| | Effluent | 7688 ± 1239 (8) (6351–10137) | 8313 ± 2302 (22) (3980–13541) | 12097 ± 4735 (30) (3450–20372) |
| | Reduction (%) | 71.62 ± 11.19 (8) (56.3–92.1) | 67.57 ± 16.76 (22) (21.2–89.6) | 63.66 ± 18.79 (30) (22.6–94.0) |
| Dissolved COD (% of Total) | Influent | 20.13 ± 17.92 (8) (4.55–81.15) | 20.30 ± 15.18 (22) (4.2–46.8) | 18.16 ± 12.03 (30) (2.5–46.7) |
| | Effluent | 86.98 ± 9.30 (8) (73.12–97.86) | 81.12 ± 13.44 (22) (51.6–98.4) | 76.16 ± 13.52 (30) (37.3–95.8) |
| TSS [mg/L] | Influent | 20447 ± 14436 (8) (6300–83500) | 29116 ± 19272 (14) (9566–76833) | 35620 ± 15792 (30) (7933–91555) |
| | Effluent | 569 ± 288 (8) (213–1173) | 1520 ± 1287 (14) (374.0–5166) | 7209 ± 5605 (30) (413.3–24000) |
| | Reduction (%) | 96.86 ± 1.91 (8) (93.2–97.0) | 91.95 ± 12.87 (14) (46.4–98.5) | 76.26 ± 20.24 (30) (26.0–99.0) |
| VSS [mg/L] | Influent | 12000 ± 7235 (8) (3466–53166) | 17656 ± 10448 (14) (5900–43750) | 19668 ± 8464 (30) (3900.0–41222) |
| | Effluent | 463.81 ± 275.25 (8) (93.3–1093) | 1457 ± 1041 (14) (533.3–3933) | 5199 ± 3871 (30) (426.7–16000) |
| | Reduction (%) | 95.98 ± 2.49 (8) (91.1–96.7) | 88.43 ± 15.74 (14) (33.3–97.4) | 69.75 ± 22.31 (30) (20.0–97.7) |

TABLE 1-continued

MEASUREMENTS OF SEWAGE UNDER DIFFERENT FLOW RATES
[x̄ ± S.D.; (N); (range)]

| Parameters Measured | | Residence Time (Hours) (Flow Rate) | | |
|---|---|---|---|---|
| | | 24 (1000 GPD) | 30 (800 GPD) | 48 (500 GPD) |
| VSS (% of TSS) | Influent | 60.04 ± 9.90 (8) (66.0–73.7) | 63.53 ± 10.97 (14) (35.47–76.76) | 55.43 ± 8.14 (30) (42.0–97.7) |
| | Effluent | 79.43 ± 20.72 (8) (86.4–80.3) | 86.85 ± 8.29 (14) (76.13–97.87) | 76.13 ± 10.90 (30) (54.9–91.2) |

As shown in Table 1, the digester was effective in reducing the total COD (the sum of particulate and soluble COD) during steady state digestion with a reduction between 64 and 72% for all flow rates. While more than 90% of the influent COD was in the form of particulate COD, more than 90% of the effluent COD was in the form of dissolved COD. VSS was also significantly reduced. Mean VSS reductions ranged between 96% and 76% for the three residence times.

TSS reductions were also significant. The mean reactor influent TSS was primarily between 1–9% TSS. The mean effluent level of total TSS was approximately 0.5 TSS (gm/L). This indicates a 95% reduction in TSS.

The reduction in both COD and TSS show the anaerobic digester has significant promise for the treatment of both wastewater sludge and wastewater streams. Surprisingly, for the three flow rates studied, the highest mean percent reduction in COD, TSS, and VSS was measured at the highest flow rate, 24 hr. Without wishing to be bound by this theory, we believe that the anaerobic digester can accomodate a flow rate that results in a 12 hr residence time, while still maintaining greater than 75% reduction in COD and greater than 90% reduction in TSS and VSS.

EXAMPLE 3

Efficiency of the Mult-Chambered Prototype Anaerobic Digester Without Addition of Sugars The prototype anaerobic digester was used as described in Example 2, except that no sugar solution was added to the contents of the digester. For the municipal wastes, a sugar addition proved unnecessary. The flow rate was 1000 GPD, or a residence time of 24 hr. Samples were analyzed for two days in July 2001. The influent temperature was about 35° C.; and the influent TSS was about 21,500 mg/L. The reduction in both total and dissolved COD was greater than 90%. For total COD, the reduction values were 95% and 97.8%. For dissolved COD, the values were 91% and 92.9%.

The reductions in both TSS and VSS were also greater than 90%. For TSS, the values were 92.2% and 93.3%. For VSS, the values were 94.6% and 96.6%.

Remarkably the values of the effluent pH was 7.5 and 6.8; while the highest effluent pH recorded when sugar was being added was 6.2. See Table 1. The alkalinity values for the effluent were also high, 1385 mg/L and 1533 mg/L; while the highest recorded when sugar was added was 1100 mg/L. This increase in pH and alkalinity would result in an increase in the production of methane and a reduction in the amount of soluble inorganics in the effluent.

Thus for this municipal waste at this ambient temperature, a sugar addition was not necessary to produce an acceptable clean effluent.

Several conclusions were drawn from these experiments. The digester functioned effectively as a treatment for primarily wastewater sludge. The digester discharged reactor effluent primarily as soluble COD. The soluble COD can be readily and easily converted by downstream aerobic processes known in the art (e.g., trickling filters, rotating biological contactors, suspended growth systems, etc.). In a preferred downstream treatment, soluble COD would be evenly discharged from the anaerobic digester to trickling filters, allowing the immediate utilization of the soluble COD effluent.

The complete disclosures of all references cited in this specification are hereby incorporated by reference. In the event of an otherwise irreconcilable conflict, however, the present specification shall control.

We claim:

1. A digester for the digestion of wastewater and sludge organic waste; said digester comprising a plurality n of at least three reaction chambers, and a settling chamber, wherein the organic waste passes through each said reaction chamber before exiting the digester, and wherein:

(a) each of said reaction chambers comprises an inlet and an outlet, and said settling chamber comprises an inlet and an outlet;

(b) each of said reaction chambers is adapted to foster the anaerobic, microbial digestion of wastewater and sludge organic waste within said chamber;

(c) the first said reaction chamber is adapted to receive an influent stream of organic waste through said inlet of the first said reaction chamber, and to transfer partially digested organic waste through said outlet of the first said reaction chamber to the inlet of the second said reaction chamber;

(d) the j-th said reaction chamber is adapted to receive, through said inlet of the j-th said reaction chamber, partially digested organic waste from said outlet of the (j−1)-st said reaction chamber; and is adapted to transfer partially digested organic waste from said outlet of the j-th said reaction chamber to said inlet of the (j+1)-st said reaction chamber, wherein j is an integer such that $1<j<n$;

(e) the n-th said reaction chamber is adapted to receive, through said inlet of the n-th said reaction chamber, partially digested organic waste from said outlet of the (n−1)-st said reaction chamber; and is adapted to transfer partially digested organic waste from said outlet of the n-th said reaction chamber to said inlet of said settling chamber;

(f) each said reaction chamber is adapted to cause, in response to a pressure differential between said inlet and said outlet of said reaction chamber, the plug flow of waste within said reaction chamber from said inlet to said outlet; with essentially no mechanical mixing other than any mixing that may be induced by gases evolved by the anaerobic, microbial digestion; and with essentially no back flow or mixing into the outlet of the prior said reaction chamber;

(g) said settling chamber is adapted to receive, through said inlet of said settling chamber, digested organic waste from said outlet of the n-th said reaction chamber; and (h) said settling chamber is adapted to cause, in response to a pressure differential between said inlet and said outlet of said settling chamber, the flow of digested waste through said settling chamber; such that essentially all suspended solids that may be present in the digested waste settle to the bottom of said settling chamber under the influence of gravity, and such that the effluent flowing through the outlet of said settling chamber is substantially depleted of any suspended solids.

2. A digester as recited in claim 1, where the volume of the first said reaction chamber is between about one-fourth and about one-half of the sum of the volumes of the second and third said reaction chambers.

3. A digester as recited in claim 1, where the inlet of said settling chamber is near the bottom of said settling chamber, wherein the outlet of said settling chamber is near the top of said settling chamber, and wherein said settling chamber comprises a series of baffles that establish a winding path for the flow of digested waste from said inlet to said outlet of said settling chamber, thereby promoting the settling by gravity of any suspended solids in the digested waste.

4. A digester as in recited in claim 1, wherein said digester lacks temperature control.

5. A digester as in claim 1, wherein the digester contains no introduced microorganisms, other than those microorganisms that are present in the input organic waste without amendment by an operator of the digester.

6. A digester as recited in claim 1, wherein the digester contains no matrix adapted for the immobilization of microorganisms.

7. A digester as recited in claim 1, wherein said reactor is made of stainless steel.

8. An anaerobic digester as recited in claim 1, wherein said reactor is made of a calcium carbonate-containing cementitious material, whereby the acidity of waste within said digester is controlled by partial neutralization of acid by the calcium carbonate.

9. A digester as recited in claim 1, additionally comprising a collector to collect any methane evolved during the anaerobic, microbial digestion of organic waste.

10. A digester as recited in claim 1, wherein said digester comprises at least four said reaction chambers.

11. A digester as recited in claim 1, wherein said reaction chambers comprise compartments within a single vessel, connected one to another to promote the serpentine flow of waste through the vessel.

12. A digester as recited in claim 1, wherein said reaction chambers comprise separate vessels linked together.

13. A method for the anaerobic digestion of wastewater and sludge organic waste; said method comprising introducing the organic waste into the inlet of the first reaction chamber of a digester as recited in claim 1, and applying sufficient pressure to the organic waste input to the first reaction chamber that the waste traverses the digester, from the inlet of the first reaction chamber to the outlet of the settling chamber, at a residence time such that the effluent from the settling chamber has at least a 70% reduction in total suspended solids as compared to the input organic waste.

14. A method as recited in claim 13, wherein the residence time is about three days or less.

15. A method as in claim 13, wherein the temperature of the digester is not controlled.

16. A method as in claim 13, additionally comprising the step of adding bacteria to the organic waste or to the digester.

17. A method as in claim 13, additionally comprising the addition of a sugar to the waste in the first reaction chamber, or prior to the first reaction chamber.

18. A method in claim 13, wherein the pH is maintained with the range from about 6 to about 8.

19. A method as recited in claim 13, wherein the residence time is about 48 hours or less.

20. A method as recited in claim 13, wherein the residence time is about 30 hours or less.

21. A method as recited in claim 13, wherein the residence time is about 24 hours or less.

22. A method as recited in claim 13, wherein the residence time is about 12 hours or less.

23. A method as recited in claim 13, additionally comprising the step of collecting any methane evolved during the anaerobic, microbial digestion of organic waste.

* * * * *